US005627037A

United States Patent [19]

Ward et al.

[11] Patent Number: 5,627,037
[45] Date of Patent: May 6, 1997

[54] ONE STEP METHOD FOR DETECTION AND ENUMERATION OF ABSOLUTE COUNTS OF ONE MORE CELL POPULATIONS IN A SAMPLE

[75] Inventors: Anthony J. Ward, San Ramon; Thomas J. Mercolino, Pleasanton; Diether J. Recktenwald, Cupertino, all of Calif.

[73] Assignee: Becton Dickinson and Company, Franklin Lakes, N.J.

[21] Appl. No.: 287,759

[22] Filed: Aug. 9, 1994

Related U.S. Application Data

[63] Continuation of Ser. No. 46,343, Apr. 8, 1993, abandoned, which is a continuation of Ser. No. 570,569, Aug. 7, 1990, abandoned.

[51] Int. Cl.$^6$ .................. G01N 33/53; G01N 33/96
[52] U.S. Cl. .......... 435/7.21; 250/459.1; 250/461.2; 436/10; 436/43; 436/63; 436/172; 436/548; 436/800; 436/805
[58] Field of Search ............... 435/7.21; 530/380; 250/459.1, 461.2; 436/10, 43, 63, 172, 548, 800, 805

[56] References Cited

U.S. PATENT DOCUMENTS

| | | | |
|---|---|---|---|
| 3,045,494 | 7/1962 | Gerarde | 73/425.6 |
| 3,433,712 | 3/1969 | Gerarde | 195/127 |
| 3,463,322 | 8/1969 | Gerarde | 210/455 |
| 3,464,800 | 9/1969 | Gerarde | 23/259 |
| 3,518,804 | 7/1970 | Gerarde | 53/37 |
| 4,110,604 | 8/1978 | Haynes et al. | 235/92 |
| 4,544,546 | 10/1985 | Wang et al. | 424/7.1 |
| 4,599,307 | 7/1986 | Saunders et al. | 435/34 |
| 4,677,061 | 6/1987 | Rose et al. | 435/39 |
| 4,704,891 | 11/1987 | Recktenwald et al. | 73/1 |
| 4,727,020 | 2/1988 | Recktenwald | 436/800 |
| 4,751,188 | 6/1988 | Valet | 436/10 |
| 4,876,189 | 10/1989 | Schetters et al. | 435/7 |
| 4,876,190 | 10/1989 | Recktenwald | 435/7.2 |
| 4,883,867 | 11/1989 | Lee et al. | 536/28 |
| 4,987,086 | 1/1991 | Brosnan et al. | 435/7.24 |
| 5,047,321 | 9/1991 | Loken et al. | 436/172 |
| 5,057,413 | 10/1991 | Terstappen et al. | 435/6 |

OTHER PUBLICATIONS

Sigma Chemical Company product catalog, (1987), p. 802.
Alosio et al., J. Immunol. methods, 128:281 (1990).

*Primary Examiner*—Christopher L. Chin
*Attorney, Agent, or Firm*—Royal N. Ronning, Jr.

[57] ABSTRACT

This invention comprises a one step method for the detection and enumeration of absolute counts of one or more cell populations in a blood sample. The method employs a reagent comprising a mixture of one or more cell markers, a fluorescent microparticle and a fixative. The reagent may be combined with unlysed whole blood and analyzed by means of flow cytometry.

17 Claims, 2 Drawing Sheets

ONE STEP METHOD FOR DETECTION AND ENUMERATION OF ABSOLUTE COUNTS OF ONE MORE CELL POPULATIONS IN A SAMPLE

This application is a continuation, of application Ser. No. 08/046,343, filed Apr. 8, 1993, now abandoned, which is a continuation of application Ser. No. 07/570,569, filed Aug. 7, 1990, now abandoned.

FIELD OF THE INVENTION

This invention relates to a one step method for determining absolute counts of cells in a sample, and more particularly, relates to a one step method for counting the absolute number of one or more populations of reticulocytes and/or leukocytes, such as $CD4^+$ lymphocytes, in a whole blood sample by means of flow cytometry.

BACKGROUND OF THE INVENTION

Counting the number and types of cells in a sample has been and continues to be an important diagnostic tool. For example, determining the number of white blood cells (or leukocytes) in a blood sample can provide an indication of infection. Determining the number of platelets, red blood cells and other hematopoietic system components (including reticulocytes) also can provide the clinician with information on the status of a patient's system. More recently, the increase in incidence of AIDS has made counting a specific population of leukocytes extremely important.

AIDS is a condition which results when an individual has become infected with HIV. Progression of the infection generally renders the individual immunodeficient, and as a result, often leads to death from lethal opportunistic infections such as *Pneumocystis carinii* pneumonia. The mechanism of HIV infection which results in AIDS is believed to be mediated through the binding of HIV to a subset of T-cells which are identified by the CD4 surface antigen. By infecting and mediating the destruction of this subset of T lymphocytes, the individual infected with HIV loses the ability to respond to opportunistic infections and pathogens.

HIV infections progress through a number of different clinical stages which may be distinguished in a variety of ways. One presently accepted classification system for charting the progress of the disease from initial exposure through the latter stages is described in the Walter Reed Classification System.

A number of criteria go into evaluating each of the several stages. For example, the presence or absence of antibodies to HIV or the presence or absence of the virus itself are used as an indication of initial exposure to HIV (WR1). Subsequently, the number of $CD4^+$ lymphocytes in the blood may be measured. A decrease in the number of $CD4^+$ lymphocytes indicates that The disease has progressed (WR3). Accordingly, accurately determining the number of $CD4^+$ lymphocytes in an AIDS patient is clinically important. (For a further description of the Walter Reed Classification System and the clinical aspects of AIDS, see Redfield et al., Sci. Amer., 259:70 (1988).)

In another example, U.S. Pat. No. 4,677,061 describes the importance of determining the ratio of specific cell types in the monitoring of autoimmune patients, particularly patients with multiple sclerosis. In this patent, the ratio of $CD4^+$ or $CD8^+$ cells to subsets thereof bearing cellular differentiation antigens is determined. Particularly useful is the ratio of $CD4^+$ to $Lp220^+$ cells.

In each instance, counting the number of cells in a given volume of blood is critical to the use of the information. Standard values for many components of the hematopoietic system are known, and it is the measurement of deviation from that standard that is of clinical significance. Accordingly, there have been developed several methods for counting such cells.

Perhaps the oldest method involves the microscopic examination of a whole blood sample (or some fraction or component thereof). The sample is placed on a slide which has been divided into specific fields, and the clinician counts the cells within each field. The method is dependent upon the skill of the clinician in counting the cells but also in distinguishing between cells types. The latter problem can be addressed by selective staining or tagging of specific cells with a variety of dyes and/or immunofluorescence markers; however, the inaccuracies due to subjectivity in manual counting cannot be avoided.

Automated counting methods have been developed in an attempt to incorporate the benefits provided by selective staining but also to reduce the error attributable to the technician. In such systems, the goal is speed with accuracy. One example of such a system involves the electronic counting of cells in a liquid sample. In this example, a known volume of liquid is sent through an instrument having a pair of electrodes. Cells of different sizes can be distinguished based upon the electrical impedance generated as each cell passes between the electrodes. U.S. Pat. No. 2,656,508 describes one system of this type.

One drawback to that system is that the relative counts of different sized particles can be determined but not the absolute counts in a specific volume. In U.S. Pat. No. 4,110,604, a method is described in which absolute counts of platelets can be determined based upon electrical impedance. The number of red blood cells is counted as is the number of platelets. Then, by knowing or determining the number of red blood cells in a given unit of volume, an equation can be used to arrive at the number of platelets in the same unit volume. Alternatively, a reference particle could be included in the sample at a known concentration, and then the reference particle is counted along with the platelets. By knowing the concentration of reference particles, one can determine the concentration of platelets.

A drawback to this system, however, is that it is most useful in distinguishing between cells based upon their physical characteristics, such as size. Not all cells are capable of discrimination based on size. For example, it is not possible to distinguish between $CD4^+$ and $CD8^+$ lymphocytes based upon size. Accordingly, other instruments (e.g., flow cytometers) have been developed that combine both measurements and correlate physical characteristics with fluorescence.

Flow cytometry comprises a well known methodology for identifying and distinguishing between different cell types in a non-homogeneous sample. The sample may be drawn from a variety of sources such as blood, lymph, urine, or may be derived from suspensions of cells from solid tissues such as brain, kidney or liver. In the flow cytometer, cells are passed substantially one at a time through one or more sensing regions where each cell is illuminated by an energy source. The energy source generally comprises means that emits light of a single wavelength in a sensing region such as that provided by a laser (e.g., He/Ne or argon) or a mercury arc lamp with appropriate bandpass filters. Different sensing regions can include energy sources that emit light at different wavelengths.

In series with each sensing region, various light collection means, such as photomultiplier tubes, are used to gather light that is refracted by each cell (generally referred to as forward light scatter), light that is reflected orthogonal to the direction of the flow of the cells through a sensing region (generally referred to as orthogonal light scatter) and one or more light collection means to collect fluorescent light that may be emitted from the cell as it passes through a sensing region and is illuminated by the energy source. Light scatter is generally correlated with the physical characteristics of each cell.

Flow cytometers further comprise data recording and storage means, such as a computer, wherein separate channels record and store the light scattered and fluorescence emitted by each cell as it passes through a sensing region (i.e., the data collected for each cell comprises a "recorded event"). By plotting orthogonal light scatter versus forward light scatter in either real time or by reanalysis of the data after the events have been recorded, one can distinguish between and count, for example, the granulocytes, monocytes and lymphocytes in a population of leukocytes. By gating on only lymphocytes, for example, using light scatter and by the use of appropriate immunofluorescence markers, such as monoclonal antibodies labelled with fluorochromes of different emission wavelength, one can further distinguish between and count cell types within the lymphocyte population (e.g., between $CD4^+$ and $CD8^+$ lymphocytes). U.S. Pat. Nos. 4,727,020, 4,704,891 and 4,599,307 describe the arrangement of the various components that comprise a flow cytometer and also the general principles of its use.

While it is possible using the above-described methods to count the number of cells in a sample and to distinguish between various cell populations, the number of cells counted will be relative (i.e., it will not give an absolute count for a specific volume of blood). Generally, these methods require that red blood cells be substantially removed from the sample. One reason is because the light scatter of the red blood cells and leukocytes is substantially overlapping making their differentiation based on light scatter alone difficult. Another reason is that in order to count leukocytes in a more rapid manner the number of red blood cells must be reduced because the number of red blood cells to leukocytes is approximately 1,000 to 1. Accordingly, practitioners in the field routinely lyse whole blood or separate out the blood cell components by density dependent centrifugation.

In addition to the step required for whole blood separation, other steps are routinely involved. For example, once a lysed blood preparation is made, immunofluorescence markers can be added. Unbound antibodies, then, are routinely washed from the cells. After that step, a fixative is added. Finally, cells are run on a flow cytometer. Each step introduces not only the possibility for error, but also the loss of cells from the sample. In addition, each step increases the risk to the technician of being exposed to contaminated blood. Using these traditional flow cytometric methods, therefore, the number of cells in a given volume of blood cannot be easily or accurately determined.

Thus, in each of the presently described systems, there are one or more obstacles that prevent one from accurately determining the absolute count of specific cells in a heterogeneous sample of blood. These obstacles are not overcome by the mere addition of a reference particle, as described in U.S. Pat. No. 4,110,604, with flow cytometry. Several drawbacks remain.

A major drawback to the use of flow cytometers is that unless the fluorescence channels and optical alignment of each flow cytometer is calibrated to read the same, there is no assurance as to the source of variation in a sample. It is likely that one instrument will give different readings on the same sample on different days if it was aligned and/or calibrated differently each day. Similarly, there is no assurance that any two instruments will provide the same results even if properly set up. Accordingly, while flow cytometry provides a better measure of identifying and distinguishing between cells in a sample, its present use as a clinical instrument is diminished by the limitations in set up and operation. What is required is a single system or method that will allow one to accurately count cells in a sample and be assured that the results from one instrument are consistent from sample to sample as well as consistent with results obtained from other instruments.

Another obstacle is to decrease or limit the exposure of the technician to an infectious sample. Traditionally, cell fixatives, such as paraformaldehyde, have been added to flow cytometry samples not only to "fix" the cell/antibody interaction but also to inactivate infectious agents that may be in the sample. Fixation traditionally has been done after staining. As a result, the technician was required to mix the sample with the immunofluorescence marker(s) and then fix. This then required separate containers for each reagent increasing the number of steps needed before a sample can be run, thus raising the possibility for error and, as importantly, the possibility for exposure.

Finally, it has be traditionally required to mix the immunofluorescence marker(s) with a small sample volume. Typically, 20 µl of reagent(s) were added to 50 µl of sample. It was believed that the total volume containing the cells and reagents should be small so that complete staining would occur.

The present invention overcomes all of these obstacles and provides a one step test for absolute counting of one or more specific populations of cells in an unlysed whole blood sample.

SUMMARY OF THE INVENTION

The invention comprises a method and kit for the absolute counting of one or more populations of cells in a sample. The preferred means for counting such cells comprises a flow cytometer. In the method, a sample is added to a tube which contains a diluent. The diluent comprises a mixture of a fixative, one or more cell markers and a known number of microparticles per unit volume. The microparticle is fluorescent and the fluorescence is distinguishable from the fluorescence emitted by the cell marker(s). The sample in the diluent then is vortexed, incubated, vortexed again and run on a flow cytometer having one or more fluorescence channels.

Fluorescence data is recorded and stored for each event. A fluorescence trigger is set for one fluorescence channel so as to include essentially all of the microparticles and cells to be counted. The number of particles then is counted by analyzing the recorded events. At least one additional fluorescence discriminator (or "gate") then is set for each population of cells in the sample such that one or more of the gates is sufficient to distinguish between the fluorescence of each population and from the microparticles. The number of cells in each population then is counted by reanalyzing the recorded events.

Knowing the number of cells in each population, the number of beads and the concentration of the beads per unit volume, the number of cells in each population can be absolutely counted.

A kit useful in the practice of this invention comprises the following items: a sample tube and a diluent wherein the diluent comprises a mixture of a fixative, one or more cell markers and a known concentration of a microparticle. The diluent may be packaged in the tube. Alternatively, the diluent may be separately contained or may be broken up into its several components each of which may be separately contained. In these alternatives, the diluent may be added to the sample tube before or after the sample is added to the tube.

DETAILED DESCRIPTION

Figure 1:
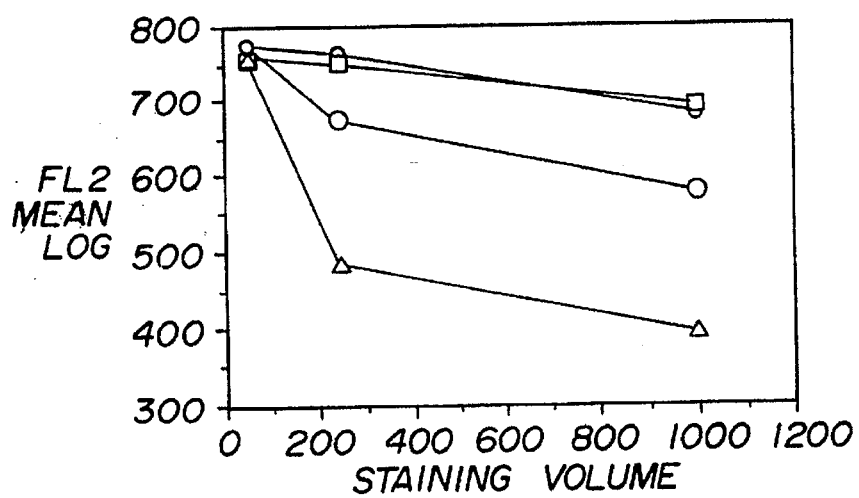
FIG. 1 comprises a plot of mean log fluorescence versus staining volume for unlysed whole blood cells stained with the same amount of Anti-Leu 3a (PE) wherein and fixed in the presence of different concentrations of fixatives.

The invention comprises a method and kit for the determining the absolute count for one or more populations of cells in a sample, preferrably, by flow cytometry. The sample may be derived from any tissue source, but generally is selected from the group consisting of unlysed whole blood, lymph, spinal fluid, urine and bone marrow. Whole blood is one preferred embodiment of the invention.

The populations of cells that can be counted in a sample comprise platelets, red blood cells, white blood cells and subsets and precursors of each. One preferred population of red blood cells comprise reticulocytes. The preferred subsets of leukocytes comprise lymphocytes, monocytes and granulocytes. In one preferred embodiment, lymphocyte subsets are particularly important and more preferred is the counting of $CD4^+$ T lymphocytes in a whole blood sample. It will be appreciated that this invention is applicable to counting any one population of cells (e.g., $CD8^+$ T lymphocytes) as well as to more than one population of cells. For example, in order to count both the number of $CD4^+$ and $CD8^+$ T lymphocytes in a sample, one could use anti-CD4 and anti-CD8 antibodies. In another example, to calculate a three part white blood cell differential, one could use anti-CD45, anti-CD14 and anti-CD15 antibodies. In still another example, to calculate the absolute number of T lymphocytes and/or B lymphocytes, one could use anti-CD3 and/or anti-CD19 (or anti-CD20) antibodies to count T cells or B cells respectively. Any population that can be identified by a single cell marker can be counted alone or can be counted with other populations in the same sample.

Cell markers useful in the practice of this invention comprise immunofluorescence markers and other fluorescence tagging agents which will specifically label one or more populations of cells. As set forth above, immunofluorescence markers comprise antibodies bound to fluorochromes. Monoclonal antibodies are preferred. Examples of fluorescence tagging agents include nucleic acid dyes, such as those described in U.S. Pat. Nos. 4,544,546, 4,883,867 and 4,937,198, and such dyes as propidium iodide, acridine orange, thiazole orange, thioflavin T and 7-aminoactinomycin D. A preferred nucleic acid dye described generally by formula I of U.S. Pat. No. 4,544,546 having a quinoline nucleus is presently marketed as a laser dye under the tradename LDS-751 (Exciton).

Fluorochromes useful in the practice of this invention may or may not be excitable at the same wavelength of light. Dyes having these properties include the phycobiliproteins (especially phycoerythrin), fluorescein derivatives (such as fluorescein isothiocyanate), peridinin chlorophyll complex (such as described in U.S. Pat. No. 4,876,190), coumarin derivatives (such as aminomethyl coumarin), pthalocyanine dyes (such as Ultralite dyes (Ultradiagnostics)) and rhodamine derivatives (such as tetramethyl rhodamine or Texas Red (Molecular Probes)).

When more than one population of cells is to be counted, more than one cell marker may be used (each being specific for a different population); however, the fluorescence of each marker must have emission wavelengths that are distinguishable not only from each other but also from the microparticle used in the diluent. When only one immunofluorescence marker is used, phycoerythrin is preferred as the fluorochrome. When two or more immunofluorescence markers are used, phycoerythrin and peridinin chlorophyll complex are preferred.

In order to count one or two populations of cells in a sample, the sample is added to a tube. The total volume of the sample plus diluent should be greater than or equal to 200 μl. A total volume of 0.5 to 1 ml is preferred. The volume of the sample then is determined by the ratio (v/v) of sample to diluent. A ratio of between 1:5 and 1:100 is preferred. A ratio of 1:9 is more preferred. Using these factors, for a 1 ml volume, 100 μl of sample in 900 μl of diluent is preferred and for a 0.5 ml volume, 50 μl of sample in 450 μl of diluent is preferred.

The tube may be made of plastic, such as polystyrene or polypropylene, or may be made of glass. To limit non-specific binding of diluent components to the tube, blocking agents (such as Bovine serum albumin ("BSA"), casein or gelatin) which bind to the ions on the surface of the tube's walls may be used. The concentration of the blocking agent should be 10–100 X the concentration of the cell marker(s). BSA is preferred as a blocking agent. These agents may be coated on and dried in the tube using a preservative such as trehalose. The tube may be of any shape or design; however, a preferred format comprise the Unopette designs (Becton Dickinson) which are further described in U.S. Pat. Nos. 3,045,494, 3,433,712, 3,463,322, 3,464,800 and 3,518,804.

It is preferred that the tube contain a diluent. It is further preferred that the sample is added to the tube containing the diluent. The diluent comprises a solution on isotonic buffer (such as phosphate buffered saline), one or more cell marker (s), a fixative (such as paraformaldehyde), and a known number of fluorescent microparticles. The fixative should be in sufficient concentration so as to not only fix the cells in the sample (thus, enabling the sample to stored, transported and run at some time well after collection) but also render inactive any virus or other infectious agent that may be present (e.g., HIV). 0.5% paraformaldehyde is preferred. It should be appreciated, however, that the fixative need not be added if the sample is to run immediately and/or the sample need not be inactivated.

The microparticle used in the practice of this invention should have certain properties. First, it should be small (i.e., between 0.2 µm and 20 µm, with 2 µm preferred) so as to stay suspended in the mixture and not settle any faster than the cells in the sample. Second, it should be made of a material that avoids clumping or aggregation. Third, it should be fluorescent. Fluorescence can be achieved by selecting the material that comprises the microparticle to be autofluorescent or it can be made fluorescent by being tagged with a fluorescent dye to appear autofluorescent. Autofluorescent microparticles are preferred.

The fluorescence of the microparticles must be such that in one fluorescence channel it is sufficiently greater than noise from background so as to be distinguishable and also must be distinguishable in other fluorescence channel(s) from the fluorescent dye(s) used as part of the immunofluorescence marker(s). One log difference between the dye(s) and the microparticle fluorescence is sufficient. Microparticles having these properties may be selected from the group consisting of fixed chicken red blood cells, coumarin beads, liposomes containing a fluorescent dye, fluorescein beads, rhodamine beads, fixed fluorescent cells, fluorescent cell nuclei, microorganisms and other beads tagged with a fluorescent dye. Coumarin beads are preferred.

The concentration of the microparticle should be greater than or equal to the number of cells to be counted. Generally, a 3:1 ratio of beads to cells is sufficient, although a 1:1 ratio is preferred.

The tube containing the sample and the diluent then is vortexed and allowed to react for a period of time which should be sufficient to cause all of the cells in the sample to be labelled by the cell marker(s). 30 minutes is preferred; however, the sample and diluent will remain stable and usable when mixed for longer periods of time before being run on a flow cytometer. The tube may be kept at room temperature during this time. The tube then is again vortexed and run on a flow cytometer.

The flow cytometer should be equipped with one or more fluorescence detectors (arbitrarily referred to as fluorescence channels 1 and 2 or "FL1" and "FL2" etc.) and with data recording and analysis means, such means generally comprising a computer. The cells are run through the flow cytometer substantially one at a time. Fluorescence and scatter data for each event is recorded. A fluorescence trigger is set such that essentially all the microparticles and cells to be counted meet or exceed the trigger level. In the preferred embodiment, the trigger is set to include at least 99% of all microparticles and cells to be counted. (This may be done manually, for example, by viewing an oscilloscope connected to the flow cytometer wherein a plot of fluorescence is made, and a line is drawn to include 99% of the microparticles.) The events then are reanalyzed, and the number of detected microparticles are then counted.

For the example where only one population of cells is being counted, a fluorescence gate is set such that the fluorescence emissions of the cells and microparticles are distinguishable. This may be in a histogram of fluorescence where the intensity of stained cells is distinguishable from the intensity of microparticles. Alternatively, and more preferably, this is done in a plot of log FL2 versus log FL1 where both the microparticles and the stained cells exceed the first fluorescence trigger in FL2 but are distinguishable by gating in FL1 versus FL2. The events stored in the computer then are reanalyzed with this second gate and the number of cells is counted. Where two populations are being counted, three fluorescence gates are set in FL1 versus FL2 such that a combination of one or more are sufficient to distinguish between the fluorescence emissions of the several populations and the microparticles.

Knowing the number of cells for any population and number of microparticles provides a ratio. Knowing the number of microparticles per unit volume and then multiplying by the first ratio provides the number of cells in a population per unit volume which is an absolute count of such cells.

Where three or more populations of cells are to be counted in a sample, the preferred method is to use at least two tubes. By way of example to calculate a three part differential for white blood cells, the antibodies anti-CD45, anti-CD14 and anti-CD15 may be used (labelling all leukocytes, all monocytes and all myeloid cells respectively). The differential is obtained by subtracting from the number of CD45 cells (i.e., the number of all white blood cells) the number of CD14 cells (i.e., the monocytes) and CD15 cells (i.e., the myeloid cells) to determine the number of lymphocytes which were not specifically labelled by an antibody but which comprise the total number of white blood cells.

In one tube, the diluent will comprise one or two of the cell markers, and in the other tube, the diluent will comprise one additional marker and may further comprise one of the markers used in the first tube. In both tubes, the diluent will include microparticles; however, it will be appreciated that if the concentration of one population is known (e.g., CD45 via the first tube), then if a labelled anti-CD45 antibody is used in the second tube without microparticles, the fluorescence trigger for the second tube may be set based upon the first tube and the concentration of the CD45 cells from the first tube is used to count the number of other cells in the second tube.

The following examples detail one or more embodiments of the invention.

The first experiment was performed to determine whether a limited sample volume of blood could be effectively stained by a fixed amount of immunofluorescence marker in a large volume of diluent. In this experiment, 50 µl of unwashed whole blood was collected and added to a tube containing a fixed amount of the anti-CD4 monoclonal, Anti-Leu 3a (available from Becton Dickinson Immunocytometry Systems "BDIS"), tagged with r-phycoerythrin ("PE"), in increasing amounts of phosphate buffered saline ("PBS"). The stained cells then were run on a FACScan brand flow cytometer (BDIS) equipped with a Hewlett-Packard 310 computer having Consort 30 or FACScan Research software (BDIS) and the mean peak fluorescence channel number was recorded for $CD4^+$ T lymphocytes. The results are presented in TABLE I.

TABLE I

| TOTAL STAINING VOLUME (µl) | MEAN PEAK CHANNEL |
|---|---|
| 55 | 799 |
| 75 | 798 |
| 175 | 793 |
| 675 | 763 |
| 3175 | 690 |

Referring to TABLE I, it was suprisingly found that the staining intensity of the $CD4^+$ T lymphocytes was not diminished when the concentration of the immunofluorescence marker decreased. Thus, at a dilution of 1:13.5 (i.e., when the volume of diluent was 625 µl), the intensity was nearly that seen under what had been previously considered to be optimal staining conditions.

In the second experiment, it was necessary to determine whether a fixed antibody would stain cells in the presence of a fixative. In this example, 50 µl of unwashed whole blood was mixed with a fixed amount of Anti-Leu 3a (PE) in the presence of PBS in either 0.5% BSA, 0.5% paraformaldehyde, 0.5% formaldehyde or 2% formaldehyde for an overall staining volume of either 50 µl, 250 µl or 1000 µl. The antibody had been previously unfixed or fixed in an identical concentration of fixative. The cells then were run as above. Mean log PE fluorescence was recorded for CD4+ T lymphocytes and plotted against the volume of the diluent for each type of fixation regime.

Referring to FIG. 1, it can be seen that all cells regardless of fixation regime gave similar fluorescence intensities at low dilutions. At higher levels of dilution, only the cells (and antibody) fixed in 0.5% paraformaldehyde gave result comparable to the unfixed cells and antibody.

From this experiment, a diluent was first prepared from a mixture of a fixed amount of Anti-Leu 3a (PE) in 0.5% paraformaldehyde, Pandex D 2.12 µ microparticles (i.e., autofluorescent coumarin beads) and 1% Pluronics F68 in PBS. The final concentration of the antibody was 0.26 ug/µl. 900 µl aliquots of this diluent were mixed with 100 µl of unlysed whole blood in a polystyrene tube and allowed to react for 30 minutes. The mixture then was vortexed again and run on a flow cytometer as above. Data was collected using FL2 as a trigger set to include greater than or equal 99% of all microparticles.

Figure 2A:
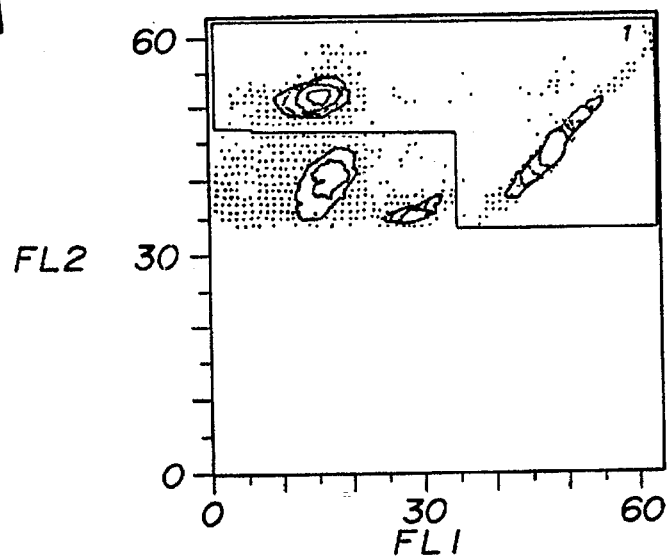
FIGS. 2A and 2B comprise 2A) a contour plot of log fluorescence 2 versus log fluorescence 1 for recorded events exceeding a first fluorescence trigger from unlysed whole blood cells stained with a diluent containing Anti-Leu 3a (PE) and Pandex D 2.12 μ autofluorescent microparticles and 2B) a histogram of log fluorescence 1 for cells and beads falling within the gate set in 2A).
Figure 2B:
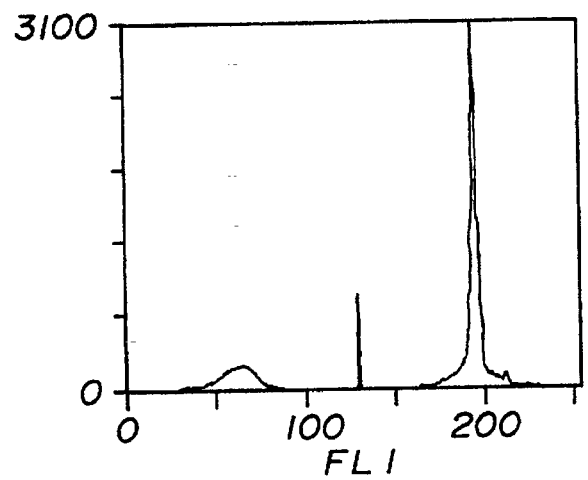

Referring to FIG. 2A, the events that exceed the fluorescence trigger (in FL2) are shown. Four populations of events can be seen: 1) microparticles; 2) CD4+ T lymphocytes; 3) CD4+ monocytes; and 4) noise (i.e., mostly red blood cells). By drawing the gate shown in FIG. 2A, the events falling within the gate (i.e.., microparticles and CD4+ T lymphocytes) can plotted in a histogram of FL1. As can be seen in FIG. 2B, two clear peaks appear in the distribution, and a fluorescence gate can be set to discriminate between the cells and the microparticles.

Figure 3:
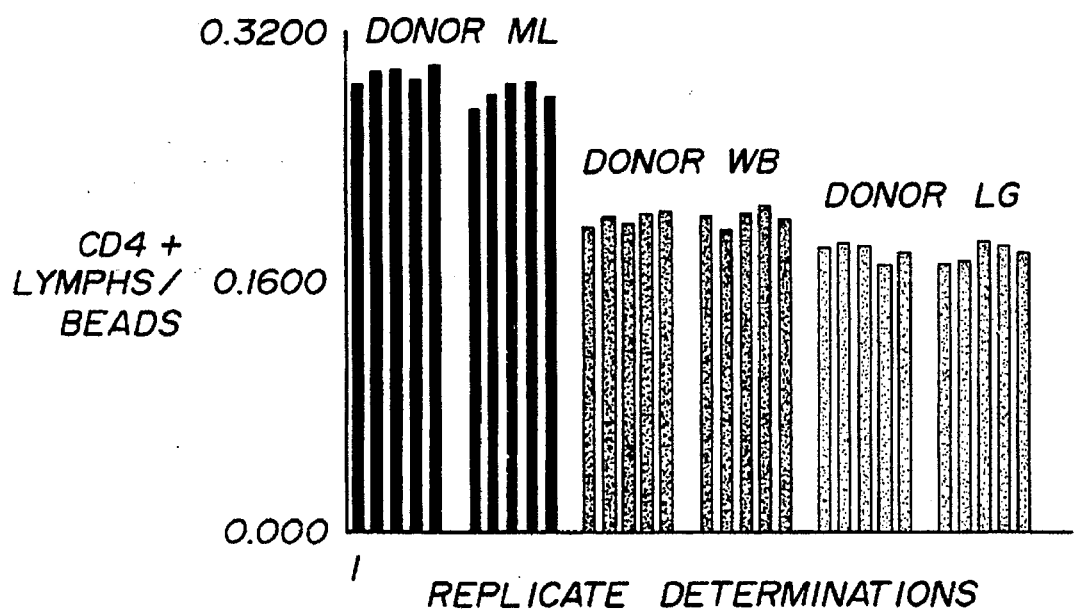
FIG. 3 comprises 5 bar graphs of the absolute number of $CD4^+$ lymphocytes per microparticle in unlysed whole blood for each of two replicate samples from three individuals which has been stained with Anti-Leu 3a (PE).

Using the diluent and methods described above, 2 replicate samples of unlysed whole blood were obtained from three different donors and from each replicate 5 separate determinations were made. The number of CD4+ T lymphocytes/microparticle then was determined. Referring to FIG. 3, it can be seen that although the absolute number of CD4+ T lymphocytes differs between individuals, the coefficient of variation between replicates and between determinations within a replicate were low (all 3% or less).

Figure 4:
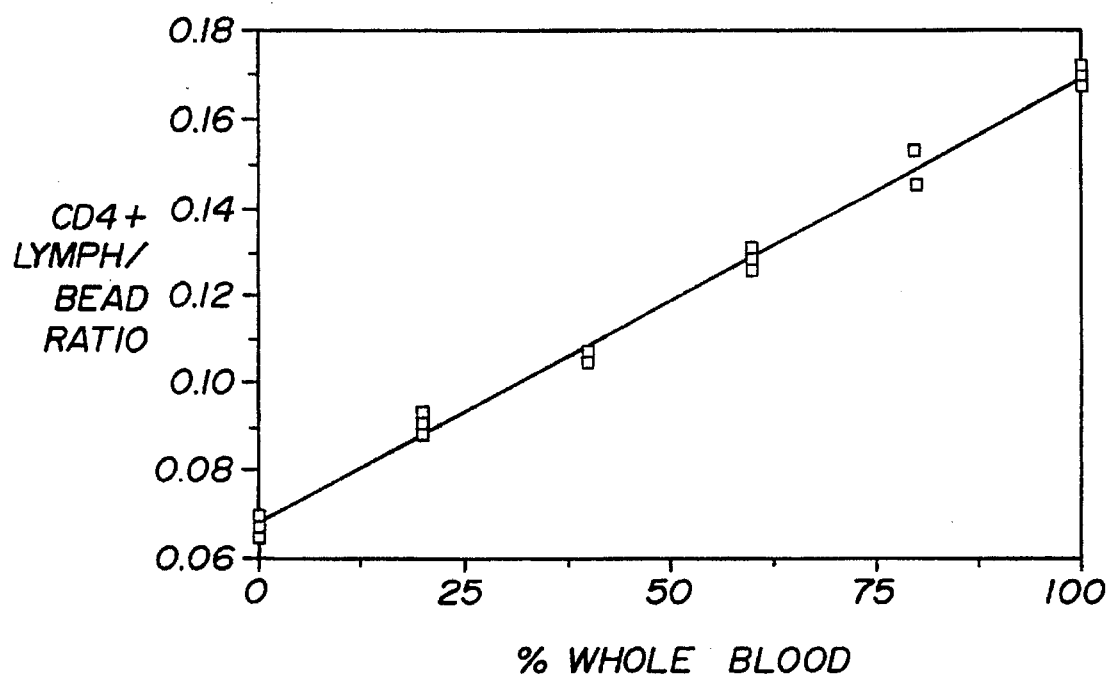
FIG. 4 comprises a plot of the ratio of $CD4^+$ lymphocytes to microparticles versus percent dilution for a buffy coat-depleted whole blood samples to which whole blood has been added back and which have been stained with Anti-Leu 3a (PE).

Finally, in order to demonstrate that the measured ratio of CD4+ T lymphocytes to microparticles is indeed a measure of absolute CD4+ T lymphocytes, buffy coat-depleted sample was prepared from a normal donor by centrifugation and aspiration. The depleted blood was mixed with whole blood from the same donor at known dilutions. The mixtures were then mixed with diluent and under the methods described above. The mixtures then were run as above, and the number of CD4+ T lymphocytes determined. Referring to FIG. 4, it can be seen that the correlation between absolute CD4+ T lymphocytes and the blood dilution was high (i.e., $r^2 = 0.996$).

Taken together, these experiments demonstrate that it is possible to determine accurately the number of cells in a sample per unit volume using a large volume of diluent and a small sample of blood.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

We claim:

1. A method for determining the absolute counts of CD4+ lymphocytes within a whole blood sample by means of flow cytometry comprising the steps of:
   (a) adding the sample to a tube containing a diluent comprising an anti-CD4 monoclonal antibody bound to phycoerythrin, paraformaldehyde and a known concentration of a 2 µm autofluorescent coumarin microparticle;
   (b) setting a fluorescence trigger in the second fluorescence channel to include at least 99% of all microparticles and CD4+ lymphocytes;
   (c) setting fluorescence gates in the first and second fluorescence channels to distinguish between the phycoerythrin fluorescence associated with the labelled CD4+ lymphocytes and the autofluorescence of the microparticle;
   (d) counting the number of CD4+ lymphocytes and microparticles from step (c); and
   (e) calculating the number of CD4+ lymphocytes per microparticle from step (d) and multiplying by the concentration of microparticles resulting in the absolute count of CD4+ lymphocytes per unit volume.

2. A method of staining cells in a sample containing said cells with one or more immunofluorescence markers, said immunofluorescence markers comprising a monoclonal antibody bound to a fluorochrome, wherein the sample is added directly to a tube containing a diluent, said diluent comprising said one or more immunofluorescence markers and a fixative.

3. The method of claim 2 wherein the fluorochromes are selected from the group consisting of phycobiliproteins, fluorescein derivatives, rhodamine, pthalocyanine derivatives, peridinin chlorophyll complex and coumarin derivatives.

4. The method of claim 3 wherein the fluorochrome is a phycobiliprotein.

5. The method of claim 4 wherein the phycobiliprotein is phycoerythrin.

6. The method of claim 2 wherein the fixative comprises the group consisting of paraformaldehyde and formaldehyde.

7. The method of claim 2 the concentration of the immunofluorescence marker is between 0.02 µg/ml and 20 µg/ml.

8. The method of claim 2 wherein the diluent further comprises a fluorescent microparticle.

9. A solution for staining cells comprising a diluent, said diluent comprising one or more immunofluorescence markers and a fixative.

10. The solution of claim 9 wherein the diluent further comprises a fluorescent microparticle.

11. The solution of claim 9 wherein the fixative is paraformaldehyde.

12. A solution for staining unlysed whole blood comprising a diluent, said diluent comprising a fluorescently labelled monoclonal antibody, a fixative and a fluorescent microparticle.

13. The solution of claim 12 wherein the antibody is an anti-CD4 monoclonal antibody.

14. The solution of claim 12 wherein the fluorescent label is phycoerythrin.

15. The solution of claim 12 wherein the fixative is paraformaldehyde.

16. The solution of claim 12 wherein the microparticle is an autofluorescent 2 µm coumarin bead.

17. A solution for staining $CD4^+$ lymphocytes in an unlysed whole blood sample wherein the solution comprises an anti-CD4 monoclonal antibody bound to phycoerythrin, paraformaldehyde and an autofluorescent 2 µm coumarin bead.

* * * * *